(12) United States Patent
Eini et al.

(10) Patent No.: US 6,432,037 B1
(45) Date of Patent: Aug. 13, 2002

(54) INTRAVAGINAL DEVICE FOR ELECTRICALLY STIMULATING AND/OR FOR SENSING ELECTRICAL ACTIVITY OF MUSCLES AND/OR NERVES DEFINING AND SURROUNDING THE INTRAVAGINAL CAVITY

(75) Inventors: Meir Eini, Nes Ziona; Dov Tamarkin, Maccabim, both of (IL)

(73) Assignee: FlexiProbe Ltd., Ramat Gan (IL)

( * ) Notice: Subject to any disclaimer, the term of this patent is extended or adjusted under 35 U.S.C. 154(b) by 17 days.

(21) Appl. No.: 09/653,263

(22) Filed: Aug. 31, 2000

(51) Int. Cl.[7] .............................. A61F 2/00; A61B 5/04; A61B 19/00
(52) U.S. Cl. ...................... 600/29; 600/373; 128/898
(58) Field of Search ............................... 600/375, 373, 600/29, 38, 41, 549; 607/138, 116; 128/898

(56) References Cited

U.S. PATENT DOCUMENTS

| | | | |
|---|---|---|---|
| 4,515,167 A | * | 5/1985 | Hockman .................. 600/549 |
| 5,010,895 A | * | 4/1991 | Maurer et al. ............. 607/138 |
| 5,255,678 A | * | 10/1993 | Deslauriers et al. ........ 600/375 |
| 5,800,501 A | * | 9/1998 | Sherlock ..................... 607/138 |

FOREIGN PATENT DOCUMENTS

FR          8309432        *  6/1983    ............ A61N/1/18

* cited by examiner

Primary Examiner—Eric F. Winakur
Assistant Examiner—Nikita Veniaminov
(74) Attorney, Agent, or Firm—G. E. Ehrlich Ltd.

(57) ABSTRACT

A device for stimulating muscles and nerves defining and surrounding an intravaginal cavity of an individual and/or for sensing electrical activity of muscles defining and surrounding an intravaginal cavity is provided. The device includes (a) a body having memory properties such that when the body is contracted and positioned within an intravaginal cavity of the individual the body self expands to conform to a contour of the intravaginal cavity; and (b) at least one pair of electrodes being attached to an exterior surface of the body such that when the body is positioned within the intravaginal cavity, each electrode of the at least one pair of electrodes is biased against a wall of the intravaginal cavity.

64 Claims, 5 Drawing Sheets

INTRAVAGINAL DEVICE FOR ELECTRICALLY STIMULATING AND/OR FOR SENSING ELECTRICAL ACTIVITY OF MUSCLES AND/OR NERVES DEFINING AND SURROUNDING THE INTRAVAGINAL CAVITY

FIELD AND BACKGROUND OF THE INVENTION

The present invention relates to an intravaginal device for electrically stimulating muscles and nerves defining and surrounding the intravaginal cavity and/or for sensing electrical activity of said muscles, and, more particularly, to a device and system utilizing same which are useful in preventing or treating urinary incontinence in women.

Urinary Incontinence

Urinary incontinence is characterized by the involuntary loss of urine in individuals. Urinary incontinence is typically brought on sphincter dysfunction or by weakening of the pelvic floor support musculature, which weakening leads to a "dropped" bladder, a condition often termed as "cystocele".

Urinary incontinence affects approximately 13 million people in the United States alone, 85% of them women. Urinary incontinence can be caused by physical stress (stress incontinence) typically brought on by heavy object lifting, coughing, laughing or sneezing, an overactive bladder (typically referred to as urge incontinence) or by an uncontrollable slow leak which is termed over flow incontinence, and which is often experienced when complete bladder emptying can not be achieved by an individual. Additional but less common types of urinary incontinence include functional incontinence and unconscious or reflex incontinence.

Of the above causes for urinary incontinence, stress incontinence and urge incontinence are considered the most prevalent. In such cases, urine loss occurs when the intravesicle pressure (i.e. pressure within the urinary bladder) exceeds, even by a small amount of pressure, the maximum urethral pressure (i.e., pressure in the urethra to maintain closure). While the problem of stress incontinence occurs in both men and women, it predominantly occurs in women of childbearing age and beyond; the frequency of incontinence in women is approximately four times that of men. Less than one-third of women with moderate to severe incontinence are treated for the problem. While 25 to 41% of all women suffer some form of incontinence, 6 to 8% are troubled by the problem to the extent that they must wear diapers or sanitary napkins constantly.

There are several exercise programs, devices, and surgical procedures which can be used to alleviate urinary incontinence.

The "kegels" exercise program is among the most basic and simple non surgical alternative for treating urinary incontinence. Such an exercise program helps to strengthen the pelvic floor muscles to thereby treat urinary incontinence. Unfortunately, many women do not perform the "kegels" exercises correctly, and as such, in most cases, no significant improvement or alleviation is achieved. In addition, recent studies have shown that the "kegels" exercise program is only effective in cases of mild to moderate urinary incontinence.

Other non surgical alternatives include diapers which simply absorb the urine involuntarily voided and as such do not alleviate the problem of incontinence. Such diapers also suffer from hygienic and aesthetic drawbacks, leakage occurs frequently, and there is no control over the voiding of urine.

A number of devices and plugs which are designed at preventing urine loss and which overcome such limitations associated with diapers have also been described in the prior art.

U.S. Pat. No. 4,457,299 to Corewell teaches an internally prestressed capsule device which is inserted into the urethra in order to aid in urinary incontinence.

U.S. Pat. No. 5,090,424 to Simon et al. describes a flexible urethral plug, designed for blocking involuntary urine flow through the urethra and assisting the natural function of the sphincter in closing the urethra.

Although such devices are functional in preventing accidental voiding of urine, they cannot be utilized to treat and/or alleviate the causes of urinary incontinence.

As such, a number of devices for treating urinary incontinence, which devices function in electrically stimulating the patient's musculature and/or monitoring muscle feedback have been described.

Electro-stimulation has been found to be effective in increasing muscle strength while biofeedback monitoring of muscular activity is valuable in assessing muscle activity and thus promoting correct pelvic floor muscle control by the patient.

U.S. Pat. No. 4,396,019 to Perry, Jr., teaches the use of an electrode-carrying insert which functions in providing the patient with feedback on muscle activity and as such enables the patient to exercise self control over the musculature contributing to urinary incontinence.

U.S. Pat. No. 4,881,526 to Johnson teaches of an intravaginal electrode and controller for preventing female urinary incontinence. The electrode includes an elongated and generally cylindrical carrier having a rounded tip, an extended lip, and a neck of reduced diameter. Motor receptor electrical stimulation signals received from the controller are coupled to the motor electrodes and directly stimulate pelvic floor musculature.

The rigid, non-yielding structure, of the above described electrode carrying devices presents several disadvantages. Since contact between a wall of the intrabody cavity and an electrode of such devices is of utmost importance for efficient muscle activation, such devices must be fabricated in a variety of sizes to fit a variety of anatomical builds. In addition, the rigid construction of such devices interferes with the physiological movement of an exercising vaginal muscle. Furthermore, the rigidity of the device greatly increases patient discomfort.

To overcome these limitations, U.S. Pat. No. 5,662,699 to Hamedi, teaches of a device which includes a flexible airtight sheath with a resilient skeleton and outer conductive bands which is collapsed by vacuum and inserted into the body cavity. When inflated within the cavity, the skeleton expands the sheath and forces the conductive bands against the body cavity wall thus ensuring optimal contact.

This device is limited to recording muscle activity, no description is provided for its ability to induce muscle stimulation. In addition, although the use of such configuration overcomes the limitations inherent to rigid electrode carrying devices, the need for an inflating/deflating mechanism greatly complicates the fabrication and application of such a device and if air leakage should occur, also its reliability in interpretation of the results.

There is thus a widely recognized need for, and it would be highly advantageous to have, an intravaginal device capable of electrically stimulating, and/or recording the activity of, the musculature/nervature defining and surrounding the intravaginal cavity and yet devoid of the above mentioned limitations of prior art designs.

SUMMARY OF THE INVENTION

According to one aspect of the present invention there is provided a device for stimulating muscles and nerves defining and surrounding an intravaginal cavity of an individual, the device comprising (a) a body having memory properties such that when the body is contracted and positioned within an intravaginal cavity of the individual the body self expands to conform to a contour of the intravaginal cavity; and (b) at least one pair of electrodes being attached to an exterior surface of the body, such that when the body is positioned within the intravaginal cavity, each electrode of the at least one pair of electrodes is biased against a wall of the intravaginal cavity to thereby maintain electrical contact with the wall. The electrical current providable from the at least one pair of electrodes serves for electrically stimulating muscles and nerves defining and surrounding the intravaginal cavity.

According to further features in preferred embodiments of the invention described below, the device further comprising a power and control unit being for providing the electrical current to the at least one pair of electrodes, the power and control unit being attachable to connectors being in electrical communication with the at least one pair of electrodes.

According to still further features in the described preferred embodiments the connectors are positioned on a region of the body such that when the body is positioned within the intravaginal cavity and attached to the power and control unit, the power and control unit is positioned outside of the intravaginal cavity.

According to still further features in the described preferred embodiments the device further comprising at least one sensor attached to the body, such that when the body is positioned within the intravaginal cavity, the at least one sensor is capable of sensing muscle activity of the muscles and nerves defining and surrounding the intravaginal cavity, so as to serve for a loop feedback or biofeedback.

According to still further features in the described preferred embodiments the at least one sensor attached to the body is a pressure sensor or an electrical activity sensor.

According to still further features in the described preferred embodiments the at least one sensor attached to the body further includes a transmitter and an internal power source.

According to still further features in the described preferred embodiments the transmitter serves for transmitting a signal receivable outside the body, the signal including data pertaining to the muscle activity sensed by the at least one sensor.

According to another aspect of the present invention there is provided a system for stimulating muscles and nerves defining and surrounding an intravaginal cavity of an individual, the system comprising: (a) an intravaginal positionable device assembly including: (i) a body having memory properties such that when the body is contracted and positioned within the intravaginal cavity of the individual the body self expands to conform to a contour of the intravaginal cavity; and (ii) at least one pair of electrodes being attached to an exterior surface of the body such that when the body is positioned within the intravaginal cavity, each electrode of the at least one pair of electrodes is biased against a wall of the intravaginal cavity to thereby maintain electrical contact with the intravaginal cavity wall, the electrical current providable from the at least one pair of electrodes serves for electrically stimulating muscles and nerves defining and surrounding the intravaginal cavity; and (iii) a power and control unit being detachably attached to the body and being for providing electrical current to the at least one pair of electrodes; and (iv) at least one sensor attached to the body, such that when the body is positioned with in the intravaginal cavity, the at least one sensor is capable of sensing muscle activity of the muscles and nerves defining and surrounding the intravaginal cavity; and (v) a transmitter being for transmitting a signal receivable outside the body, the signal including data pertaining to the muscle activity sensed by the at least one sensor; and (b) an extracorporeal monitoring unit being for processing the signal received from the transmitter to thereby determine duration or intensity of the electrical current provided to the at least one pair of electrodes from the power and control unit.

According to yet another aspect of the present invention there is provided a method of stimulating muscles and nerves defining and surrounding an intravaginal cavity of an individual, the method comprising the steps of: (a) positioning an intravaginal device within the intravaginal cavity of the individual, the intravaginal device including: (i) a body having memory properties such that when the body is contracted and positioned within an intravaginal cavity of the individual the body self expands to conform to a contour of the intravaginal cavity; and (ii) at least one pair of electrodes being attached to an exterior surface of the body such that when the body is positioned within the intravaginal cavity, each electrode of the at least one pair of electrodes is biased against a wall of the intravaginal cavity to thereby maintain electrical contact with the wall, wherein the electrical current providable from the at least one pair of electrodes serves for electrically stimulating muscles and nerves defining and surrounding the intravaginal cavity; and (b) providing the electrical current of a predetermined intensity and/or duration to the at least one pair of electrodes attached to the exterior surface of the body to thereby stimulate muscles and nerves defining and surrounding the intravaginal cavity of the individual.

According to still further features in the described preferred embodiments the system serves for treating or preventing urinary incontinence in the individual.

According to still further features in the described preferred embodiments the body is constructed of an elastic material selected from the group consisting of silicon, rubber and latex. Other flexible materials are also envisaged.

According to still further features in the described preferred embodiments a width of the body when relaxed is at least 1.3–1.5 times larger than the width of the body when fully contracted.

According to still further features in the described preferred embodiments a length of the body when relaxed is 1.3–1.7, preferable 1.5, times shorter than the length of the body when fully contracted.

According to still further features in the described preferred embodiments the at least one pair of electrodes include a conductive material selected from the group consisting of gold and platinum.

According to still further features in the described preferred embodiments the at least one sensor attached to the body is a pressure sensor or an electrical activity sensor.

According to still further features in the described preferred embodiments the power and control unit includes a receiver for receiving command signal from the extracorporeal unit, the command signals serving for modulating the duration or the intensity of the electrical current provided to the at least one pair of electrodes from the power and control unit.

According to still further features in the described preferred embodiments the body defines a substantially rounded diamond shaped frame when relaxed.

According to still further features in the described preferred embodiments stimulation of the muscles and nerves defining and surrounding the intravaginal cavity serves for treatment or prevention of urinary incontinence in the individual.

According to another aspect of the present invention there is provided a device for sensing electrical activity of muscles defining and surrounding an intravaginal cavity of an individual, the device comprising (a) a body having memory properties such that when the body is contracted and positioned within an intravaginal cavity of the individual the body self expands to conform to a contour of the intravaginal cavity; and (b) at least one pair of electrodes being attached to an exterior surface of the body such that when the body is positioned within the intravaginal cavity, each electrode of the at least one pair of electrodes is biased against a wall of the intravaginal cavity to thereby maintain electrical contact with the wall.

The present invention successfully addresses the shortcomings of the presently known configurations by providing an intravaginal device for stimulating the muscles and nerves defining and surrounding the intravaginal cavity and/or for sensing electrical activity of said muscles, which device can be fitted to a wide range of anatomical builds, is easy to position while remaining at the desired location and orientation within the intravaginal cavity, and yet minimizes patient discomfort when utilized.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
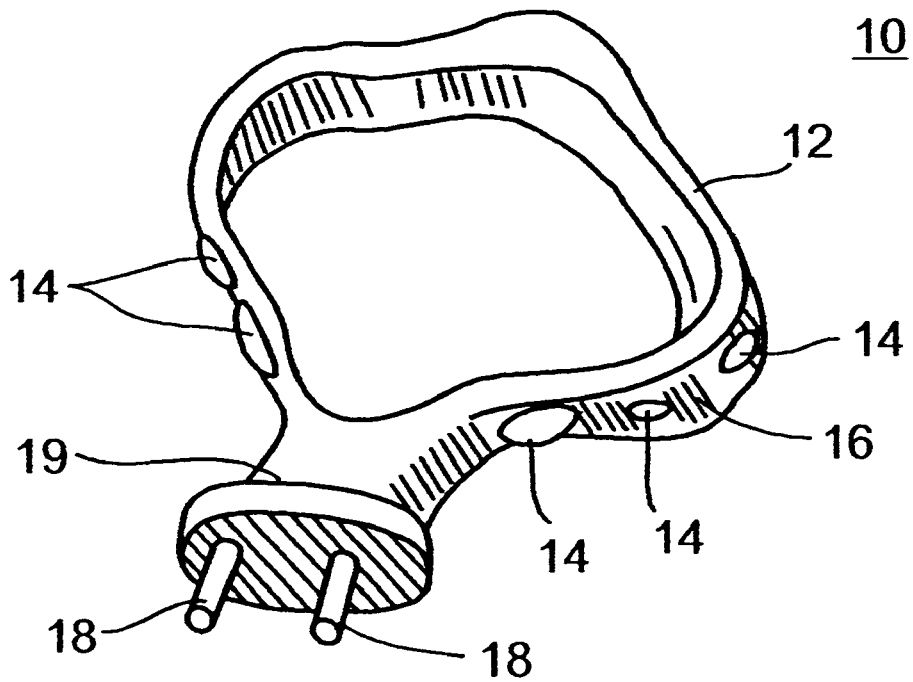
FIG. 1 is a perspective view of a device for stimulating muscles and nerves defining or surrounding the intravaginal cavity and/or sensing activity of said muscles, according to the teachings of the present invention.
Figure 2:
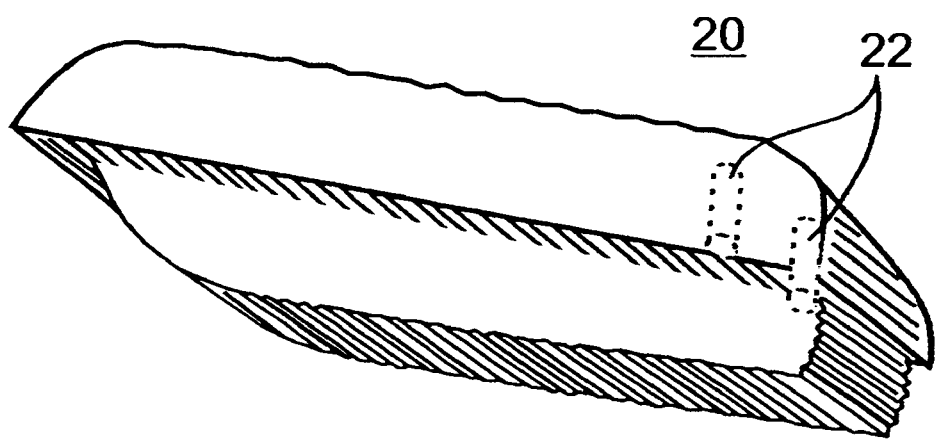
FIG. 2 a perspective view of a power and control unit attachable to the device described in FIG. 1.

The present invention is of an intravaginal device, which can be used to electrically stimulate the muscles and nerves defining and surrounding the intravaginal cavity and/or sense, record and report of the muscles electrical activity. Specifically, the present invention can be used to treat female urinary incontinence by electrically stimulating the muscles responsible for such a condition and/or by monitoring the activity of such muscles so as to serve information to a biofeedback system.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates one possible configuration of a device for stimulating, and/or sensing electrical activity of, muscles and nerves defining and surrounding an intravaginal cavity of an individual, which is referred to hereinunder as device 10.

Figure 4A:
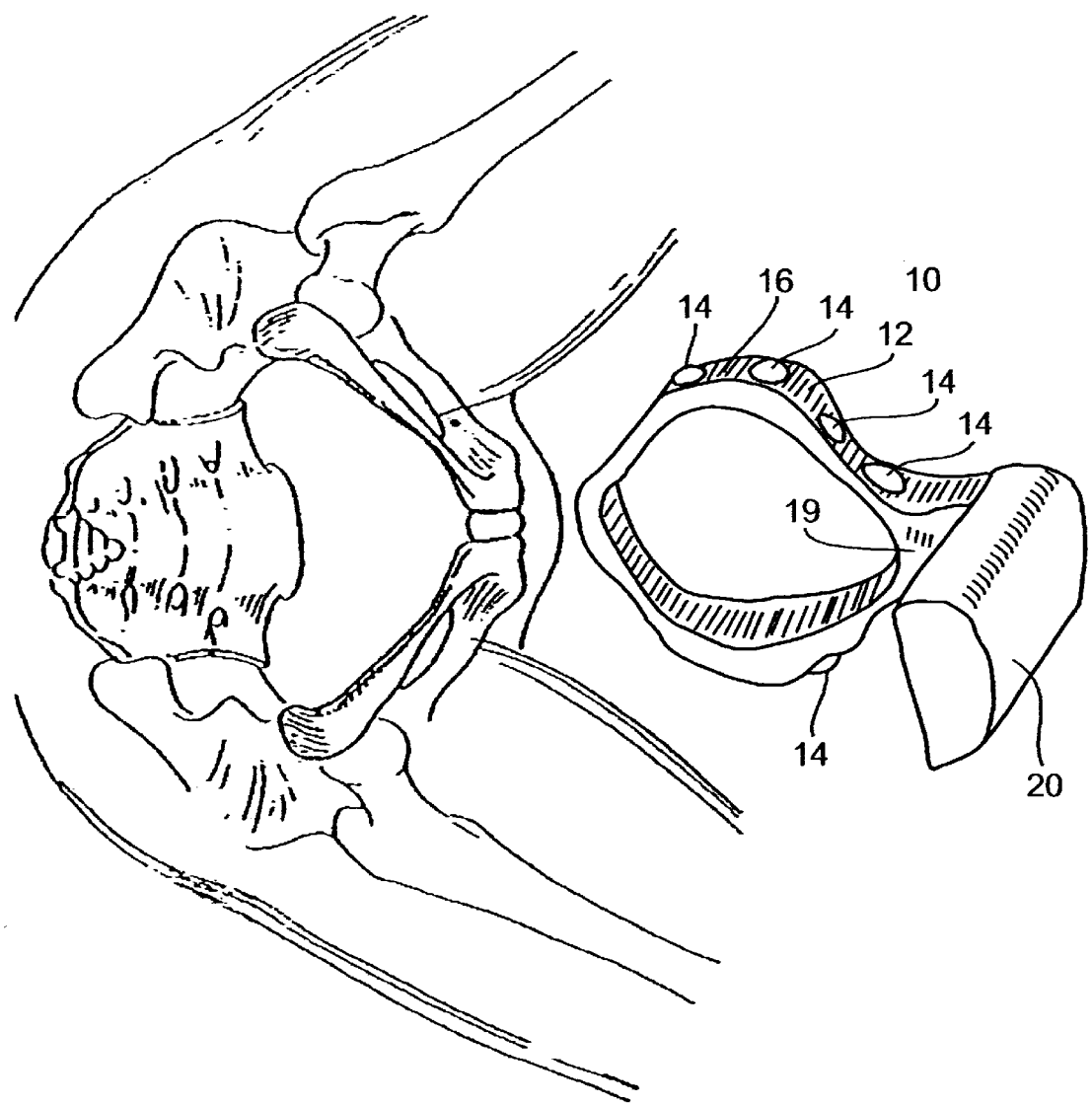
FIGS. 4a–b demonstrate the process of inserting and positioning the device for stimulating muscles and nerves defining or surrounding the intravaginal cavity, and/or sensing activity of said muscles, according to the teachings of the present invention.
Figure 4B:
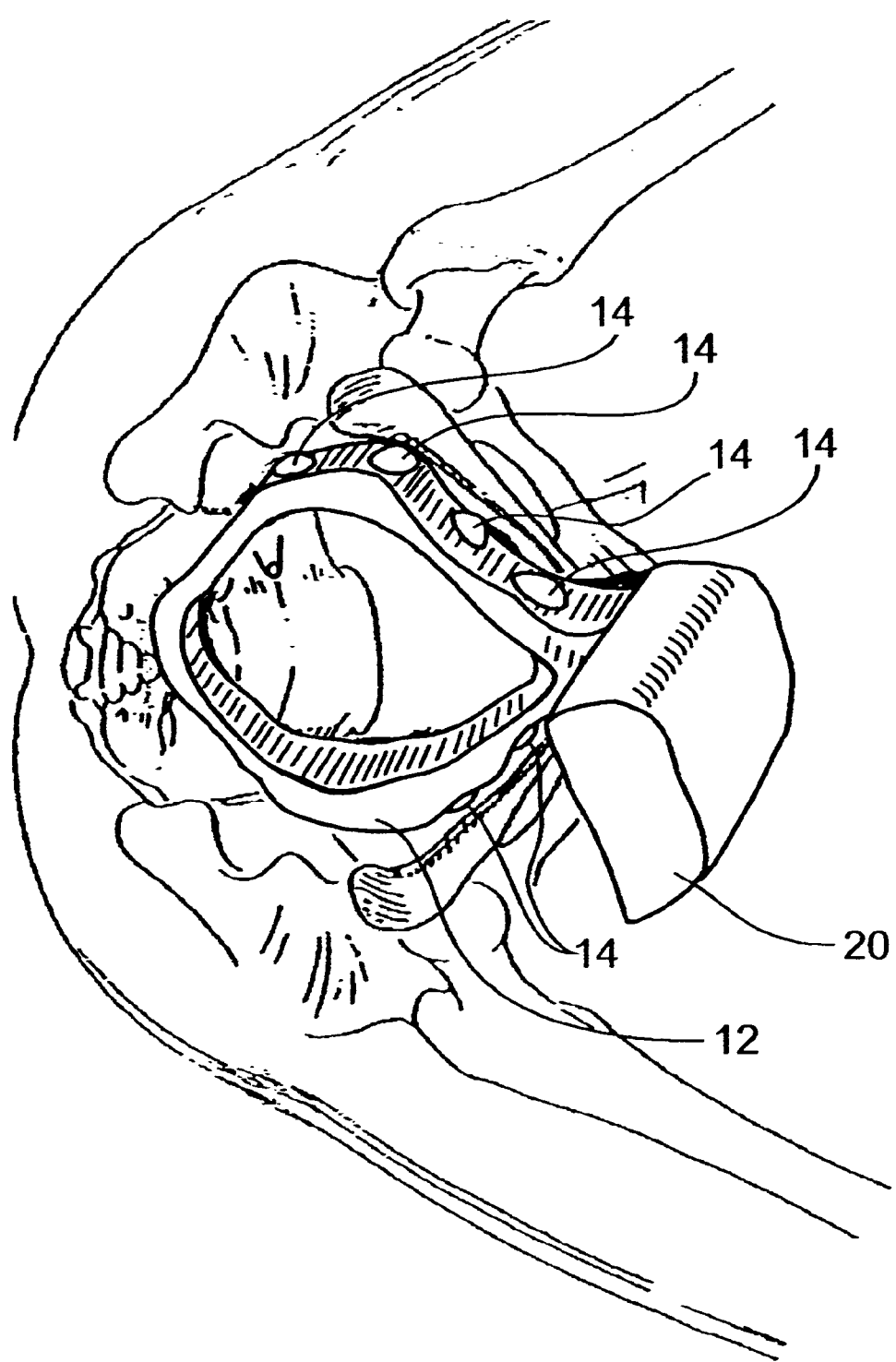

Device 10 includes a body 12. Body 12 is constructed such that when contracted and positioned within an intravaginal cavity of the individual (see FIGS. 4a–b), body 12 self expands to conform to a contour of the intravaginal cavity. This memory (self expansion) property of body 12 can be achieved by fabricating at least a portion of body 12 from an elastic material having such memory, such as, but not limited to, silicon, rubber, latex, or alternatively, by providing various springed hinge points along body 12 which allow contracting of body 12 against a force of a spring, thus allowing body 12 to self expand following contraction.

Figure 3:
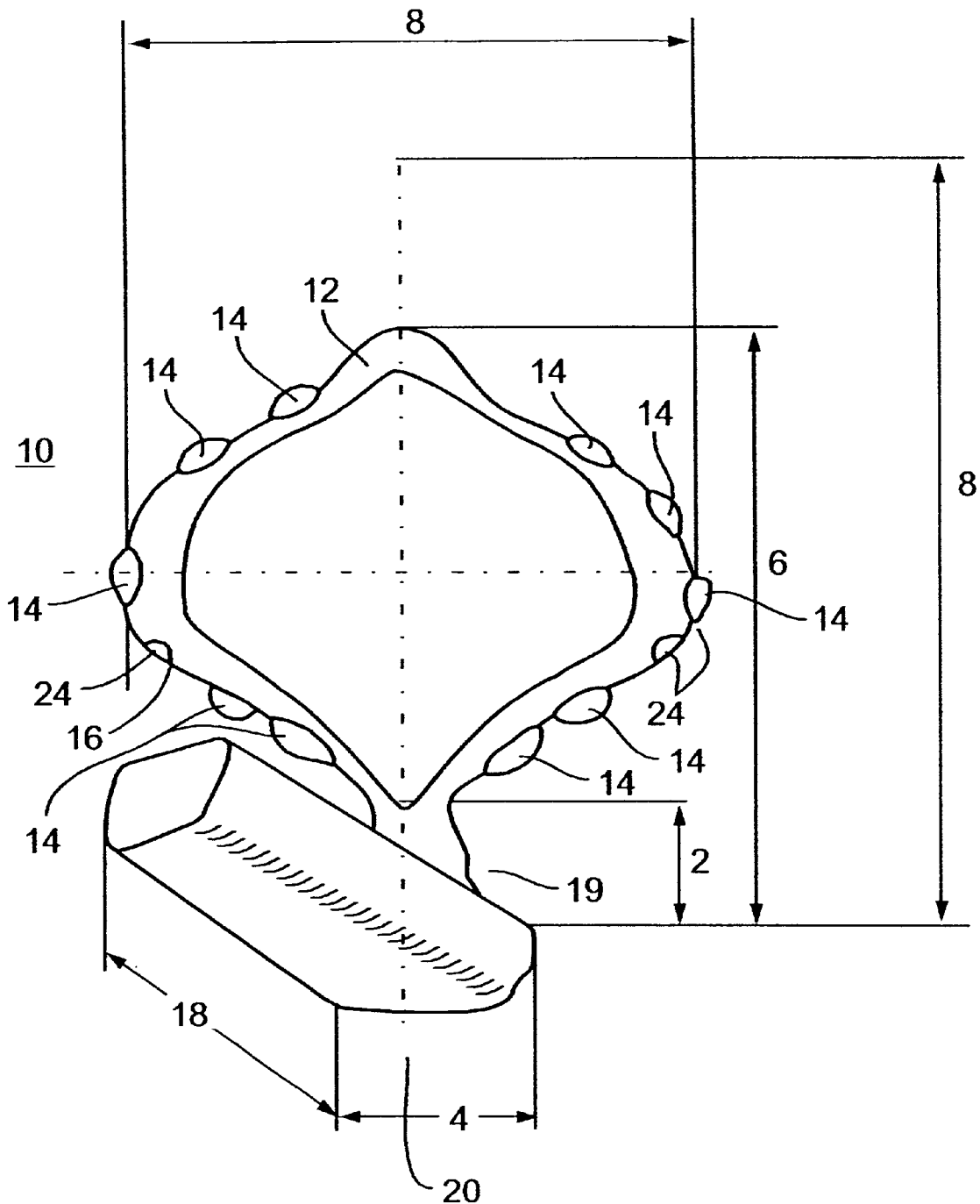
FIG. 3 is a side view of the device shown in FIG. 1 connected to the power and control unit shown in FIG. 2.

As best seen in FIG. 3, device 10 further includes at least one pair of electrodes 14. In one embodiment of the present invention some or all of electrodes 14 serve for providing an electrical current to the walls of the intravaginal cavity of the individual. In another embodiment of the present invention some or all of electrodes 14 serve for recording electrical activity of the muscles defining the walls of the intravaginal cavity of the individual. In either case, electrodes 14 are preferably attached to an exterior surface 16 of body 12. Thus, when body 12 is positioned within the intravaginal cavity, each electrode 14 is biased against a wall of the intravaginal cavity to thereby maintain electrical contact with the wall. To maintain optimal electrical conductance, the portion of electrodes 14 which maintains contact with the intravaginal cavity wall is fabricated from a material such as, but not limited to, gold and platinum, or any other highly conductive material.

It will be appreciated that when expanding to its relaxed state, body 12 causes reduction (anatomical repositioning) of prolapsed intravaginal tissue and therefore, to the benefit of more physiological muscular exercising. The flexibility of body 12 in itself, as opposed to rigid constructions, also adds to achieving more physiological muscular exercising.

The electrical current providable from electrodes 14 serves for electrically stimulating muscles and/or nerves defining and surrounding the intravaginal cavity. Preferably, such muscles include, the pelvic floor muscles, the weakening of which contributes to the onset and progression of urinary incontinence. Other muscles defining the cavity are not excluded. Such nerves include those which control the functionality of the bladder, dysfunction thereof may also lead to incontinence. Thus, by stimulating such musculature and/or nervature, device 10 of the present invention can be utilized to prevent or treat urinary incontinence. It will be appreciated that strengthening the pelvic floor muscles also improves the ability to experience stronger and longer orgasms when engaged in sexual activity.

Since the position of these muscles, in relation to the intravaginal cavity varies from one individual to the next, placement of electrodes 14 upon exterior surface 16 is of crucial importance when wanting to achieve maximal stimulation/activity records in each individual. It will further be appreciated that although optimal placement of electrodes 14 can be achieved by testing the device on a large number of individuals, such anatomical limitations can be traversed by placing several pairs of electrodes 14 upon exterior surface 16, thus enabling the activation of one or more specific pairs of electrodes 14 according to individual anatomical built. This may also be advantageous in cases wherein muscles of one side of the intravaginal cavity are stronger then the muscles of the other side, as is typically the case in birth related incontinence. Thus, muscle stimulation with the device of the present invention may be applied preferentially or solely to the weak muscles, as opposed to all of the muscles surrounding and defining the vaginal cavity.

As shown in FIGS. 1 and 3, one possible configuration of body 12 is a substantially rounded diamond shaped frame of approximately 5–7 cm in length and 7–9 cm in width in its relaxed state. In this configuration, electrodes 14 are preferably positioned on exterior surface 16 of the members defining such a frame.

The construction of body 12 is selected such that when relaxed it is 1.3–1.7, preferable 1.5, times shorter than when fully contracted. Similarly, the width of body 12 is selected such that when relaxed is at least 1.3–1.7, preferable 1.5, times larger than when fully contracted. This enables body 12 to be utilizable in a wide range of anatomical builds.

Device 10 further includes connectors 18, which serve for electrically interfacing with a power and control unit which is further described below.

Preferably, connectors 18 are positioned on a neck 19 of body 12 such that when body 12 is positioned within the intravaginal cavity and attached to the power and control unit, the power and control unit is positioned outside of the intravaginal cavity.

Thus, as is specifically shown in FIGS. 2–5, device 10 further includes a power and control unit 20 which serves for providing electrical currents or to electrodes 14 and/or for creating a potential difference therebetween. Power and control unit 20 includes receptacles 22 which serve for interfacing with connectors 18 described above.

Power and control unit 20 preferably also includes an attachment mechanism for securing power and control unit 20 to the underwear or body of the individual when device 10 is in use. This ensures that body 12 does not translate or rotate inside the intravaginal cavity when in use, thus guarantying optimal electrical contact and stimulation of the desired muscles. Such attachment mechanism can includes Velcro™ fasteners for securing power and control unit 20 to the underwear or pubic hair of the individual, or it can include sticky tape or suction cups for securing power and control unit 20 against the body of the individual.

Power and control unit includes a power source, such as a battery, a control unit for controlling the output from the power source and the required circuitry. Power and control unit 20 preferably also includes a processing unit as is further detailed hereinbelow.

Power and control unit 20 preferably also includes exterior controls for controlling the intensity and duration of the electrical current provided to electrodes 14.

For example, an individual or a treating physician can set the power and control unit according to individual needs in order to effectively stimulate and thus contract and exercise the musculature defining or surrounding the intravaginal cavity.

Preferably, electrical current is provided from power and control unit 20 in an intermittent pattern which includes 1–20, preferably 2–10 seconds intervals each providing alternating current spaced by 2–40, preferably 4–20 seconds of rest intervals.

As shown in FIG. 3, according to a preferred embodiment of the present invention device 10 further includes at least one sensor 24 (two are shown in FIG. 3) which is preferably attached to exterior surface 16 of body 10. Sensor(s) 24 serve for sensing muscle activity of the muscles defining and surrounding the intravaginal cavity. Such sensing can be either prior to, during or following stimulation of these muscles via electrodes 14.

Sensor(s) can be either pressure sensors, or sensors which are capable of sensing muscle electrical activity (e.g., surface electromyography sensors). It will be appreciated that, in the latter case a grounding electrode must be included in device 10. Both these sensor types have been previously used with biofeedback intravaginal devices and are therefore well known.

In any case, sensors 24 serve to evaluate muscle activity prior to, during or following treatment to thereby serve as either a basis for a treatment regimen or as feedback to a treatment regimen.

According to one preferred embodiment of the present invention, sensors 24 interface with power and control unit 20 via connectors 18 or any other dedicated connectors preferably positioned at neck 19. To this end, sensors 24 are provided with power from power and control unit 20 and also communicate information relating to muscle activity to power and control unit 20.

Such information received by power and control unit 20 can be processed by a processing unit contained therein and the processed information utilized to automatically adjust or set the intensity and/or duration of the electrical current provided from power and control unit 20 to electrodes 14.

It will be appreciated that power and control unit 20 can also include a memory device and ports for interfacing with a personal computer such that sensor information of each treatment session which is collected by power and control unit 20 can be uploaded onto a computer for storage and/or further analysis.

This configuration of device 10 of the present invention is particularly advantageous since it enables device 10 to set the most suitable course of treatment for an individual.

Alternatively, the sensor provided information can be transmitted to an extracorporeal unit for analysis via a transmitter included within sensor(s) 24 or body 12 or preferably within power and control unit 20.

Figure 5:
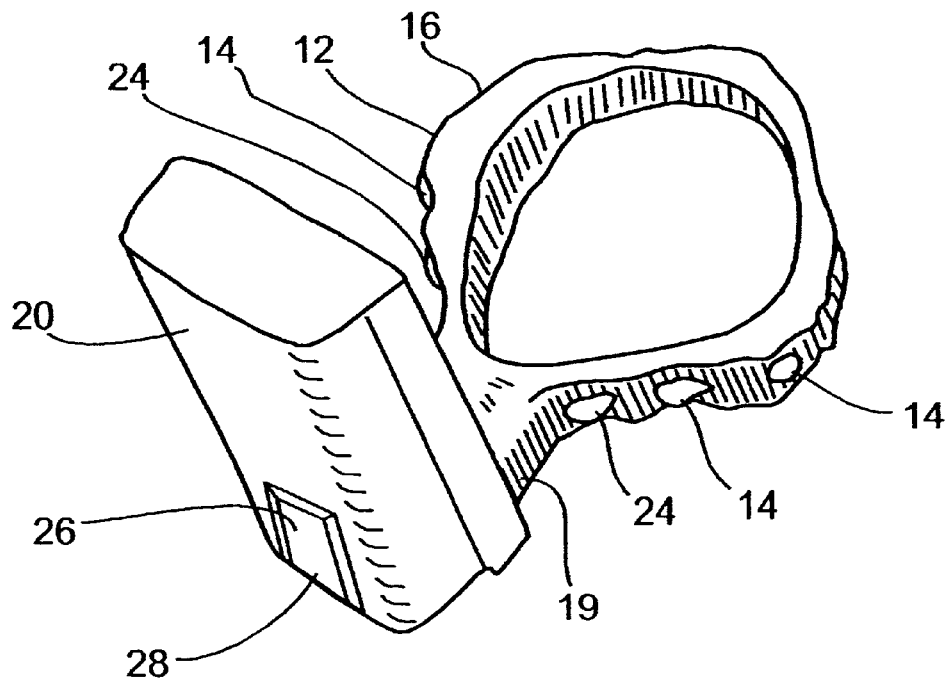
FIG. 5 shows a system in accordance with the teachings of the present invention.
Figure 5:
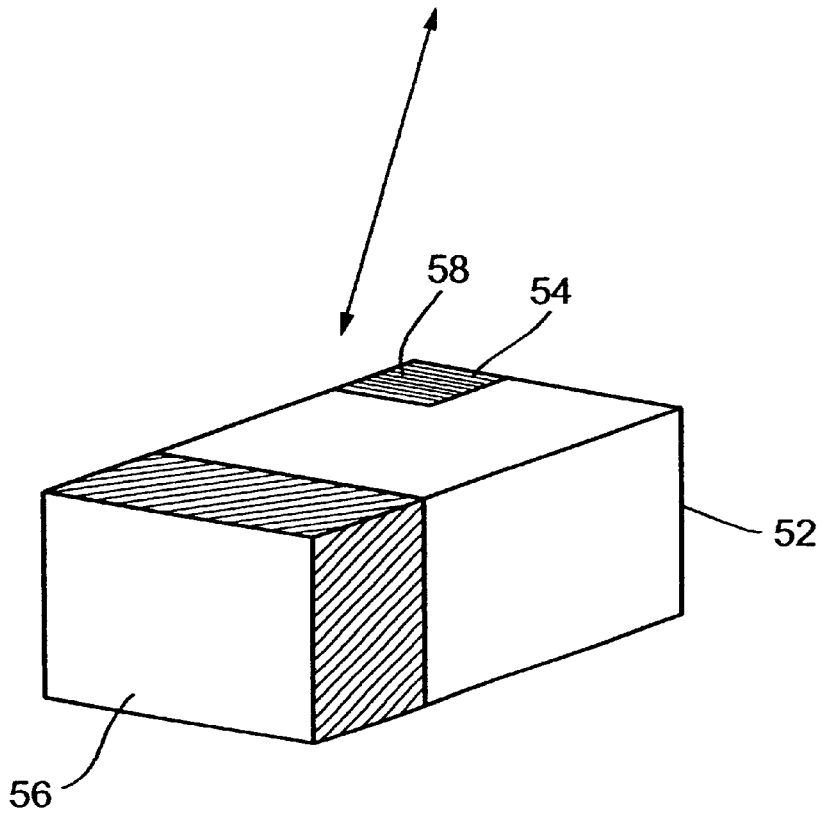

Thus, according to another aspect of the present invention and as shown in FIG. 5, device 10 of the present invention can form a part of a system for stimulating muscles and nerves defining and surrounding an intravaginal cavity of an individual, which is referred to hereinunder as system 50.

System 50 includes device 10 as described above, which according to this aspect of the present invention includes a transmitter 26 preferably positioned on or in power and control unit 20. Transmitter 26 serves for transmitting a signal receivable outside the body, which signal includes data pertaining to muscle activity sensed by sensor(s) 24.

System 50 also includes an extracorporeal unit 52 which serves for processing the signal received from transmitter 26 to thereby determine duration or intensity of the electrical current provided to electrodes 24 from power and control unit 20. To this end, extracorporeal unit includes a receiver 54 and a processing unit 56 (e.g., a personal computer).

Preferably, power and control unit 20 of device 10 also includes a receiver 28, such that following processing of the signal received from transmitter 26, extracorporeal unit 52 preferably transmits, via a transmitter 58, a command signal receivable by receiver 28, which command signal determines the duration or intensity of the electrical current provided to electrodes 24 from power and control unit 20.

It will be appreciated that this configuration of system 50 is advantageous since extracorporeal unit 52 enables a more accurate processing of the information collected by sensor(s) 24 to thereby more accurately determine a suitable course of treatment. In addition, this configuration of system 50 also enables processing and storing of information collected from several treatment sessions conducted over any period of time of say weeks or months. Furthermore, statistical analysis of information collected from several individuals can be utilized to improve treatment regimens or to improve the construction of device 10.

Thus, the present invention provides a device utilizable for electrically stimulating the muscles and nerves defining and surrounding the intravaginal cavity. In sharp distinction to prior art devices, some of which are described in the background section hereinabove, the present invention present a simple solution for traversing the inherent limitations of prior art devices. By virtue of it's memory properties, the device according to the teachings of the invention: (i) self conforms to the anatomy of a wide range of individuals thus maintaining optimal contact between the electrodes provided thereupon and the wall of the intravaginal cavity; (ii) it can be easily applied to, and removed from, the intravaginal cavity; and (iii) it remains at the desired location within the intravaginal cavity without producing discomfort.

This enables accurate stimulation of the muscles and nerves defining and surrounding the intravaginal cavity which is particularly useful for treatment or prevention of urinary incontinence, a condition characterized by involuntary loss of urine which is often caused by (i) weakness or inactivity of these muscles; and/or (ii) imbalance of the autonomic nervous system versus the parasympathetic system, which is a cause of bladder dysfunction, both may benefit by such stimulation.

Thus the electro-stimulation and biofeedback monitoring providable by the device of the present invention can be utilized to effectively increase muscle strength while assessing muscle activity and prescribing the best course of treatment for the individual treated.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for stimulating muscles and nerves defining and surrounding an intravaginal cavity of an individual, the device comprising:
   (a) a body having memory properties such that when said body is contracted and positioned within an intravaginal cavity of the individual said body self expands to conform to a contour of the intravaginal cavity; and
   (b) at least one pair of electrodes being attached to an exterior surface of said body such that when said body is positioned within the intravaginal cavity, each electrode of said at least one pair of electrodes is biased against a wall of the intravaginal cavity to thereby maintain electrical contact with said wall, wherein an electrical current providable from said at least one pair of electrodes serves for electrically stimulating the muscles and nerves defining and surrounding the intravaginal cavity;
wherein a length of said body when relaxed is 1.3–1.7 times shorter than said length of said body when fully contracted.

2. The device of claim 1, wherein the device serves for treating or preventing urinary incontinence in the individual.

3. The device of claim 1, further comprising a power and control unit being for providing said electrical current to said at least one pair of electrodes, said power and control unit being attachable to connectors being in electrical communication with said at least one pair of electrodes.

4. The device of claim 3, wherein said connectors are positioned on a region of said body such that when said body is positioned within the intravaginal cavity and attached to said power and control unit, said power and control unit is positioned outside of the intravaginal cavity.

5. The device of claim 3, wherein said power and control unit further includes a controller for controlling duration and/or intensity of electrical currents provided therefrom to said at least one pair of electrodes.

6. The device of claim 1, wherein said body is constructed of an elastic material selected from the group consisting of, rubber, latex and silicon.

7. The device of claim 1, wherein a width of said body when relaxed is at least 1.3–1.5 times larger than said width of said body when fully contracted.

8. The device of claim 1, wherein said at least one pair of electrodes includes an electrically conductive material selected from the group consisting of gold and platinum.

9. The device of claim 1, further comprising at least one sensor attached to said body, such that when said body is positioned within the intravaginal cavity, said at least one sensor is capable of sensing muscle activity of the muscles defining and surrounding the intravaginal cavity.

10. The device of claim 9, wherein said at least one sensor attached to said body is a pressure sensor or an electrical activity sensor.

11. The device of claim 9, wherein said at least one sensor attached to said body further includes a transmitter.

12. The device of claim 11, wherein said transmitter serves for transmitting a signal receivable outside the body, said signal including data pertaining to said muscle activity sensed by said at least one sensor.

13. The device of claim 1, wherein said body defines a substantially rounded diamond shaped frame when relaxed.

14. A system for stimulating muscles and nerves defining and surrounding an intravaginal cavity of an individual, the system comprising:
   (a) an intravaginal positionable device assembly including:
      (i) a body having memory properties such that when said body is contracted and positioned within the intravaginal cavity of the individual said body expands to conform to a contour of the intravaginal cavity; and
      (ii) at least one pair of electrodes being for providing an electrical current, said at least one pair of electrodes being attached to an exterior surface of said body such that when said body is positioned within the intravaginal cavity, each electrode of said at least one pair of electrodes is biased against a wall of the intravaginal cavity to thereby maintain electrical contact with the intravaginal cavity wall, said electrical current providable from said at least one pair of electrodes serves for electrically stimulating muscles and nerves defining and surrounding the intravaginal cavity; and
      (iii) a power and control unit being detachably attached to said body and being for providing electrical current to said at least one pair of electrodes; and
      (iv) at least one sensor attached to said body, such that when said body is positioned within the intravaginal cavity, said at least one sensor is capable of sensing muscle activity of the muscles and nerves defining and surrounding the intravaginal cavity; and
      (v) a transmitter being for transmitting a signal receivable outside the body, said signal including data pertaining to said muscle activity sensed by said at least one sensor; and
   (b) an extracorporeal monitoring unit being for processing said signal received from said transmitter to thereby determine duration or intensity of said electrical current provided to said at least one pair of electrodes from said power and control unit;
wherein a length of said body when relaxed is 1.3–1.7 times shorter than said length of said body when fully contracted.

15. The system of claim 14, wherein the system serves for treating or preventing urinary incontinence in the individual.

16. The system of claim 14, wherein said body is constructed of an elastic material selected from the group consisting of silicon, rubber and latex.

17. The system of claim 14, wherein a width of said body when relaxed is at least 1.3–1.5 times larger than said width of said body when fully contracted.

18. The system of claim 14, wherein said at least one pair of electrodes include a conductive material selected from the group consisting gold and platinum.

19. The system of claim 14, wherein said at least one sensor attached to said body is a pressure sensor or an electrical activity sensor.

20. The system of claim 14, wherein said power and control unit includes a receiver for receiving command signal from said extracorporeal unit, said command signals serving for modulating said duration or said intensity of said electrical current provided to said at least one pair of electrodes from said power and control unit.

21. The system of claim 14, wherein said body defines a substantially rounded diamond shaped frame when relaxed.

22. A method of stimulating muscles and nerves defining and surrounding an intravaginal cavity of an individual, the method comprising the steps of:
   (a) positioning an intravaginal device within the intravaginal cavity of the individual, said intravaginal device including:
      (i) a body having memory properties such that when said body is contracted and positioned within an intravaginal cavity of the individual said body self expands to conform to a contour the intravaginal cavity, wherein a length of said body when relaxed is 1.3–1.7 times shorter than said length of said body when fully contracted; and
      (ii) at least one pair of electrodes being for providing an electrical current, said at least one pair of electrodes being attached to an exterior surface of said body such that when said body is positioned within the intravaginal cavity, each electrode of said at least one pair of electrodes is biased against a wall of the intravaginal cavity to thereby maintain electrical contact with said wall, wherein said electrical current providable from said at least one pair of electrodes serves for electrically stimulating muscles and nerves defining and surrounding the intravaginal cavity; and
   (b) providing said electrical current of a predetermined intensity and/or duration to said at least one pair of electrodes attached to said exterior surface of said body to thereby stimulate muscles and nerves defining and surrounding the intravaginal cavity of the individual.

23. The method of claim 22, wherein stimulation of the muscles and nerves defining and surrounding the intravaginal cavity serves for treatment or prevention of urinary incontinence in the individual.

24. A device for sensing electrical activity of muscles defining and surrounding an intravaginal cavity of an individual, the device comprising:
   (a) a body having memory properties such that when said body is contracted and positioned within an intravaginal cavity of the individual said body self expands to conform to a contour of the intravaginal cavity; and
   (b) at least one pair of electrodes being attached to an exterior surface of said body such that when said body is positioned within the intravaginal cavity, each electrode of said at least one pair of electrodes is biased against a wall of the intravaginal cavity to thereby maintain electrical contact with said wall;
wherein a length of said body when relaxed is 1.3–1.7 times shorter than said length of said body when fully contracted.

25. The device of claim 24, wherein the device serves for treating or preventing urinary incontinence in the individual.

26. The device of claim 24, further comprising a power and control unit being attachable to connectors being in electrical communication with said at least one pair of electrodes.

27. The device of claim 26, wherein said connectors are positioned on a region of said body such that when said body is positioned within the intravaginal cavity and attached to said power and control unit, said power and control unit is positioned outside of the intravaginal cavity.

28. The device of claim 24, wherein said body is constructed of an elastic material selected from the group consisting of, rubber, latex and silicon.

29. The device of claim 24, wherein a width of said body when relaxed is at least 1.3–1.5 times larger than said width of said body when fully contracted.

30. The device of claim 24, wherein said at least one pair of electrodes includes an electrically conductive material selected from the group consisting of gold and platinum.

31. The device of claim 24, wherein said at least one pair of electrodes serve for sensing muscle activity of the muscles defining and surrounding the intravaginal cavity.

32. The device of claim 24, wherein said body defines a substantially rounded diamond shaped frame when relaxed.

33. A device for stimulating muscles and nerves defining and surrounding an intravaginal cavity of an individual, the device comprising:
(a) a body having memory properties such that when said body is contracted and positioned within an intravaginal cavity of the individual said body self expands to conform to a contour of the intravaginal cavity; and
(b) at least one pair of electrodes being attached to an exterior surface of said body such that when said body is positioned within the intravaginal cavity, each electrode of said at least one pair of electrodes is biased against a wall of the intravaginal cavity to thereby maintain electrical contact with said wall, wherein an electrical current providable from said at least one pair of electrodes serves for electrically stimulating the muscles and nerves defining and surrounding the intravaginal cavity;
wherein said body defines a substantially rounded diamond shaped frame when relaxed.

34. The device of claim 33, wherein the device serves for treating or preventing urinary incontinence in the individual.

35. The device of claim 33, further comprising a power and control unit being for providing said electrical current to said at least one pair of electrodes, said power and control unit being attachable to connectors being in electrical communication with said at least one pair of electrodes.

36. The device of claim 35, wherein said connectors are positioned on a region of said body such that when said body is positioned within the intravaginal cavity and attached to said power and control unit, said power and control unit is positioned outside of the intravaginal cavity.

37. The device of claim 35, wherein said power and control unit further includes a controller for controlling duration and/or intensity of electrical currents provided therefrom to said at least one pair of electrodes.

38. The device of claim 33, wherein said body is constructed of an elastic material selected from the group consisting of rubber, latex and silicon.

39. The device of claim 33, wherein a width of said body when relaxed is at least 1.3–1.5 times larger than said width of said body when fully contracted.

40. The device of claim 33, wherein a length of said body when relaxed is 1.3–1.7 times shorter than said length of said body when fully contracted.

41. The device of claim 33, wherein said at least one pair of electrodes includes an electrically conductive material selected from the group consisting of gold and platinum.

42. The device of claim 33, further comprising at least one sensor attached to said body, such that when said body is positioned within the intravaginal cavity, said at least one sensor is capable of sensing muscle activity of the muscles defining and surrounding the intravaginal cavity.

43. The device of claim 42, wherein said at least one sensor attached to said body is a pressure sensor or an electrical activity sensor.

44. The device of claim 42, wherein said at least one sensor attached to said body further includes a transmitter.

45. The device of claim 44, wherein said transmitter serves for transmitting a signal receivable outside the body, said signal including data pertaining to said muscle activity sensed by said at least one sensor.

46. A system for stimulating muscles and nerves defining and surrounding an intravaginal cavity of an individual, the system comprising:
(a) an intravaginal positionable device assembly including:
(i) a body having memory properties such that when said body is contracted and positioned within the intravaginal cavity of the individual said body expands to conform to a contour of the intravaginal cavity; and
(ii) at least one pair of electrodes being for providing an electrical current, said at least one pair of electrodes being attached to an exterior surface of said body such that when said body is positioned within the intravaginal cavity, each electrode of said at least one pair of electrodes is biased against a wall of the intravaginal cavity to thereby maintain electrical contact with the intravaginal cavity wall, said electrical current providable from said at least one pair of electrodes serves for electrically stimulating muscles and nerves defining and surrounding the intravaginal cavity; and
(iii) a power and control unit being detachably attached to said body and being for providing electrical current to said at least one pair of electrodes; and
(iv) at least one sensor attached to said body, such that when said body is positioned within the intravaginal cavity, said at least one sensor is capable of sensing muscle activity of the muscles and nerves defining and surrounding the intravaginal cavity; and
(v) a transmitter being for transmitting a signal receivable outside the body, said signal including data pertaining to said muscle activity sensed by said at least one sensor; and
(b) an extracorporeal monitoring unit being for processing said signal received from said transmitter to thereby determine duration or intensity of said electrical current provided to said at least one pair of electrodes from said power and control unit;
wherein said body defines a substantially rounded diamond shaped frame when relaxed.

47. The system of claim 46, wherein the system serves for treating or preventing urinary incontinence in the individual.

48. The system of claim 46, wherein said body is constructed of an elastic material selected from the group consisting of silicon, rubber and latex.

49. The system of claim 46, wherein a width of said body when relaxed is at least 1.3–1.5 times larger than said width of said body when fully contracted.

50. The system of claim 46, wherein a length of said body when relaxed is 1.3–1.7 times shorter than said length of said body when fully contracted.

51. The system of claim 46, wherein said at least one pair of electrodes include a conductive material selected from the group consisting gold and platinum.

52. The system of claim 46, wherein said at least one sensor attached to said body is a pressure sensor or an electrical activity sensor.

53. The system of claim 46, wherein said power and control unit includes a receiver for receiving command signal from said extracorporeal unit, said command signals serving for modulating said duration or said intensity of said electrical current provided to said at least one pair of electrodes from said power and control unit.

54. A method of stimulating muscles and nerves defining and surrounding an intravaginal cavity of an individual, the method comprising the steps of:

(a) positioning an intravaginal device within the intravaginal cavity of the individual, said intravaginal device including:
  (i) a body having memory properties such that when said body is contracted and positioned within an intravaginal cavity of the individual said body self expands to conform to a contour the intravaginal cavity, wherein said body defines a substantially rounded diamond shaped frame when relaxed; and
  (ii) at least one pair of electrodes being for providing an electrical current, said at least one pair of electrodes being attached to an exterior surface of said body such that when said body is positioned within the intravaginal cavity, each electrode of said at least one pair of electrodes is biased against a wall of the intravaginal cavity to thereby maintain electrical contact with said wall, wherein said electrical current providable from said at least one pair of electrodes serves for electrically stimulating muscles and nerves defining and surrounding the intravaginal cavity; and
(b) providing said electrical current of a predetermined intensity and/or duration to said at least one pair of electrodes attached to said exterior surface of said body to thereby stimulate muscles and nerves defining and surrounding the intravaginal cavity of the individual.

55. The method of claim 54, wherein stimulation of the muscles and nerves defining and surrounding the intravaginal cavity serves for treatment or prevention of urinary incontinence in the individual.

56. A device for sensing electrical activity of muscles defining and surrounding an intravaginal cavity of an individual, the device comprising:
  (a) a body having memory properties such that when said body is contracted and positioned within an intravaginal cavity of the individual said body self expands to conform to a contour of the intravaginal cavity; and
  (b) at least one pair of electrodes being attached to an exterior surface of said body such that when said body is positioned within the intravaginal cavity, each electrode of said at least one pair of electrodes is biased against a wall of the intravaginal cavity to thereby maintain electrical contact with said wall;
wherein said body defines a substantially rounded diamond shaped frame when relaxed.

57. The device of claim 56, wherein the device serves for treating or preventing urinary incontinence in the individual.

58. The device of claim 56, further comprising a power and control unit being attachable to connectors being in electrical communication with said at least one pair of electrodes.

59. The device of claim 58, wherein said connectors are positioned on a region of said body such that when said body is positioned within the intravaginal cavity and attached to said power and control unit, said power and control unit is positioned outside of the intravaginal cavity.

60. The device of claim 56, wherein said body is constructed of an elastic material selected from the group consisting of rubber, latex and silicon.

61. The device of claim 56, wherein a width of said body when relaxed is at least 1.3–1.5 times larger than said width of said body when fully contracted.

62. The device of claim 56, wherein a length of said body when relaxed is 1.3–1.7 times shorter than said length of said body when fully contracted.

63. The device of claim 56, wherein said at least one pair of electrodes includes an electrically conductive material selected from the group consisting of gold and platinum.

64. The device of claim 56, wherein said at least one pair of electrodes serve for sensing muscle activity of the muscles defining and surrounding the intravaginal cavity.

* * * * *